United States Patent
May et al.

(10) Patent No.: US 7,458,975 B2
(45) Date of Patent: Dec. 2, 2008

(54) METHOD OF REPLACING AN ANTERIOR CRUCIATE LIGAMENT IN THE KNEE

(75) Inventors: Thomas C. May, Wrentham, MA (US); Gregory Whittaker, Stoneham, MA (US)

(73) Assignee: Johnson & Johnson, New Brunswick, NJ (US)

( * ) Notice: Subject to any disclaimer, the term of this patent is extended or adjusted under 35 U.S.C. 154(b) by 711 days.

(21) Appl. No.: 11/018,457

(22) Filed: Dec. 21, 2004

(65) Prior Publication Data
US 2006/0149283 A1   Jul. 6, 2006

(51) Int. Cl.
A61B 17/56 (2006.01)
A61B 17/04 (2006.01)
A61F 2/08 (2006.01)

(52) U.S. Cl. .................. 606/53; 606/60; 606/232; 606/329; 623/13.14; 623/908; 623/911; 128/898

(58) Field of Classification Search ... 623/13.14–13.17, 623/908, 911; 606/53, 60, 300, 301, 329, 606/86 R, 232
See application file for complete search history.

(56) References Cited

U.S. PATENT DOCUMENTS

| | | | |
|---|---|---|---|
| 5,139,520 A | 8/1992 | Rosenberg | |
| 5,266,075 A | 11/1993 | Clark et al. | |
| 5,393,302 A | 2/1995 | Clark et al. | |
| 5,573,538 A | 11/1996 | Laboureau | |
| 5,601,562 A | 2/1997 | Wolf et al. | |
| 5,769,894 A | 6/1998 | Ferragamo | |
| 5,913,433 A | 6/1999 | Whelan | |
| 6,132,433 A | 10/2000 | Whelan | |
| 6,254,073 B1 | 7/2001 | Noniewicz et al. | |
| 6,371,124 B1 | 4/2002 | Whelan | |
| 6,499,486 B1 * | 12/2002 | Chervitz et al. | 128/898 |
| 6,517,546 B2 | 2/2003 | Whittaker et al. | |
| 6,537,319 B2 | 3/2003 | Whelan | |
| 6,623,524 B2 | 9/2003 | Schmieding | |
| 6,712,849 B2 | 3/2004 | Re et al. | |
| 6,733,529 B2 | 5/2004 | Whelan | |
| 6,752,830 B1 | 6/2004 | Goble et al. | |
| 6,780,188 B2 | 8/2004 | Clark et al. | |
| 7,032,599 B2 * | 4/2006 | May et al. | 128/898 |
| 2001/0044627 A1 | 11/2001 | Justin | |
| 2001/0053934 A1 | 12/2001 | Schmieding | |
| 2002/0156476 A1 | 10/2002 | Wilford | |
| 2002/0173849 A1 | 11/2002 | MxcKernan et al. | |
| 2003/0050642 A1 | 3/2003 | Schmieding | |

(Continued)

FOREIGN PATENT DOCUMENTS

EP    1180351    2/2002

Primary Examiner—Suzette J Gherbi

(57) ABSTRACT

A method of reconstructing a ruptured anterior cruciate ligament in a human knee. Femoral and tibial tunnels are drilled into the femur and tibia. A transverse tunnel is drilled into the femur to intersect the femoral tunnel. A filamentary loop is threaded through the femoral tunnel and tibial tunnel and partially through the transverse tunnel. A replacement graft is formed into a loop and moved into the tibial tunnels using a surgical needle and suture. A flexible filamentary member is simultaneously moved along with the loop into the femoral and transverse tunnels. The filamentary member is used as a guide wire in the transverse tunnel to insert a cannulated cross-pin to secure a top of the looped graft in the femoral tunnel.

6 Claims, 15 Drawing Sheets

U.S. PATENT DOCUMENTS

| | | |
|---|---|---|
| 2003/0065391 A1 | 4/2003 | Re et al. |
| 2003/0120343 A1 | 6/2003 | Whelan |
| 2003/0130666 A1 | 7/2003 | Whittaker et al. |
| 2003/0176919 A1 | 9/2003 | Schmieding |
| 2004/0059415 A1 | 3/2004 | Schmieding |
| 2004/0092936 A1* | 5/2004 | Miller et al. .................. 606/72 |
| 2004/0097977 A1 | 5/2004 | Goble et al. |
| 2004/0172034 A1 | 9/2004 | Re et al. |
| 2004/0193167 A1 | 9/2004 | Tucciarone et al. |
| 2004/0194789 A1 | 10/2004 | Whelan |
| 2004/0225358 A1 | 11/2004 | Goble et al. |
| 2004/0230302 A1 | 11/2004 | May et al. |
| 2004/0254585 A1 | 12/2004 | Whittaker et al. |
| 2005/0203623 A1* | 9/2005 | Steiner et al. ............ 623/13.14 |

* cited by examiner

METHOD OF REPLACING AN ANTERIOR CRUCIATE LIGAMENT IN THE KNEE

TECHNICAL FIELD

The field of art to which this invention relates is arthroscopic surgical procedures, in particular, arthroscopic surgical procedures for replacing an anterior cruciate ligament in the knee.

BACKGROUND OF THE INVENTION

Arthroscopic surgical repairs of a ruptured anterior cruciate ligament in the knee are known in this art. A rupture of the anterior cruciate ligament ("ACL") is often seen in sports related injuries. In a typical arthroscopic procedure, the surgeon prepares the patient for surgery by insufflating the patient's knee with sterile saline solution. Several cannulas are inserted into the knee and used as entry portals into the interior of the knee. A conventional arthroscope is inserted through one of the cannulas so that the knee may be remotely viewed by the surgeon. The surgeon then drills a tibial tunnel and a femoral tunnel in accordance with conventional surgical techniques using conventional surgical drills and drill guides. A replacement anterior cruciate ligament graft is then prepared and mounted in the tibial and femoral tunnels, and secured using conventional techniques and known devices in order to complete the ACL reconstruction.

Several types of anterior cruciate ligament grafts are available for use by the surgeon in ACL reconstruction procedures. The grafts may be autografts that are harvested from the patient, for example patellar bone-tendon-bone grafts, or hamstring grafts. Or the grafts can be xenografts, allografts, or synthetic polymer grafts.

There are various known methods for securing the femoral end of an ACL graft in the femoral tunnel. The methods include, for example, cross-pinning, and the use of femoral tunnel interference screws. Of particular interest is a procedure wherein a cross-pin is used to secure the graft in the femoral tunnel. When such a device is used, a transverse tunnel is drilled into a section of the femur such that it intersects the longitudinal femoral tunnel. When using a conventional cross-pinning technique, the surgeon typically prepares the graft by forming or folding it into a loop. Typically, this step is preceded by whip stitching the ends of the graft in a conventional manner. After the top end of the graft loop is emplaced in the femoral tunnel, a cross-pin is then inserted into the transverse tunnel and through the opening in the loop of the graft underneath the top of the graft, thereby both securing the graft in place in the femoral tunnel.

Although the existing methods of performing ACL reconstruction using cross-pins are satisfactory for their intended purpose, and provide the patient with the desired therapeutic result, there is a constant need in this art for improved methods of performing ACL graft reconstruction using cross-pins. In particular, one critical aspect of a cross-pinning method is the ability to place a graft in a femoral tunnel such that when the cross-pin is inserted through the transverse tunnel, the pin is precisely placed in the opening of the graft loop below the top of the graft loop. It can be appreciated by those skilled in this art that placement of the cross-pin above the top of the graft loop will result in the graft not being adequately secured in the femoral tunnel, with the likelihood of a catastrophic failure. Precise placement of a cross-pin into the opening of a graft loop is presently accomplished in this art by using guide wires and cannulated cross-pins that are inserted over the guide wires. In one known method, a guide wire consisting of a flexible filamentary member is actually looped through the transverse tunnel and down through the femoral and tibial tunnels, such that an end extends out through both sides of the transverse tunnel, and a bottom loop extends out through the bottom of the tibial tunnel. A graft is folded to form a graft loop and placed about the bottom loop of the guide wire such that the guide wire runs through the graft loop opening. The ends of the guide wire extending out through the openings of the transverse tunnel are tensioned to pull the guide wire and graft up through the tibial and femoral tunnels into a desired position for fixation, and a cannulated cross-pin is then threaded over the guide wire and mounted in the transverse tunnel to secure the upper part of the graft loop in the femoral tunnel. Although this method succeeds in emplacing a graft in the femoral tunnel and securing it with a cross-pin, there are disadvantages associated with its use. For example, it requires that the graft be pulled longitudinally through the tibial and femoral tunnels by pulling transversely on the flexible filamentary member ends that exit the sides of the transverse tunnel. This may result in damage to the bone surrounding the interiors of the femoral and transverse tunnels. In addition, it can be a lengthy and time-consuming process since it is inefficient to move a graft longitudinally through a tunnel by pulling transversely on the flexible filamentary member.

Accordingly, there is a need in this art for improved methods of ACL knee reconstruction using cross-pins.

SUMMARY OF THE INVENTION

It is an object of the present invention to provide a novel method of performing an ACL reconstruction using a cannulated cross-pin, wherein a filamentary member is provided as a guide for the cross-pin, and an ACL graft is pulled into the tibial and femoral tunnels using a surgical needle and attached surgical suture.

Therefore, a method for repairing a knee arthroscopically using an anterior cruciate ligament replacement graft is disclosed. The method consists of providing an anterior cruciate ligament replacement graft that is formed into a loop having a top and a bottom. The loop has an opening. A longitudinal tibial tunnel is drilled through a top of a tibia adjacent to the knee, the tibial tunnel has top and bottom openings. A longitudinal femoral tunnel is drilled through the bottom section of an adjacent femor such that the tibial tunnel and the femoral tunnel are substantially in alignment. The femoral tunnel has opposed top and bottom openings. A substantially transverse tunnel is drilled through the femoral tunnel such that the transverse tunnel intersects the femoral tunnel and is in communication therewith, the transverse tunnel has opposed first and second openings. A filamentary member is provided. The filamentary member is an endless loop. The filamentary member is threaded through knee such that a first end loop of the filamentary member extends out from a first side of the transverse tunnel, continues through the femoral and tibial tunnels, and a second end loop extends out through the bottom opening of the tibial tunnel. A surgical needle and suture are provided. The suture is mounted to the surgical needle such that a suture loop is formed. The graft is engaged with the suture loop such that the suture passes through the graft loop opening. And, the graft is also engaged with the second end loop of the filamentary member such that the filamentary member passes through the graft loop opening. The needle and suture are moved into the tibial tunnel and femoral tunnel. The graft loop is pulled into and partially out of the tibial tunnel by pulling on the needle and suture, such that the top of the graft loop is located outside of the top opening of the tibial tunnel and adjacent to the bottom opening of the femoral tunnel. The needle and suture move out through the top opening of the femoral tunnel. The filamentary member simultaneously moves with the graft as the suture is pulled. The second end loop of the filamentary member is also located outside of the top opening of the tibial tunnel adjacent to the bottom opening of the femoral tunnel. The first end loop of the filamentary member is then cut to form first and second ends. The first end of the filamentary member is maintained outside of the first opening of the tibial tunnel, and the filamentary member is manipulated to extend through the transverse tunnel with the second end of the filamentary member extending out through the second opening of the transverse tunnel. The suture is then tensioned to move the top of the graft loop and the second end loop of the filamentary member into to femoral tunnel such that the graft loop opening is in substantial alignment with the transverse tunnel. The filamentary member is tensioned to form a substantially straight configuration that is substantially in alignment with the transverse tunnel. A cannulated cross-pin is provided. The upper end of the graft loop is secured in the femoral tunnel by passing the cannulated bone pin over the filamentary member and mounting the bone pin in the transverse tunnel. The lower end of the graft loop may be secured in the tibial tunnel by inserting a securement member or device into the tibial tunnel, e.g. an interference screw, thereby completing the reconstruction.

These and other aspects, advantages of the present invention, will become more apparent from the following drawings and accompanying description.

DESCRIPTION OF THE INVENTION

The terms "anterior cruciate ligament" and the acronym "ACL" are used interchangeably herein.

Figure 1:
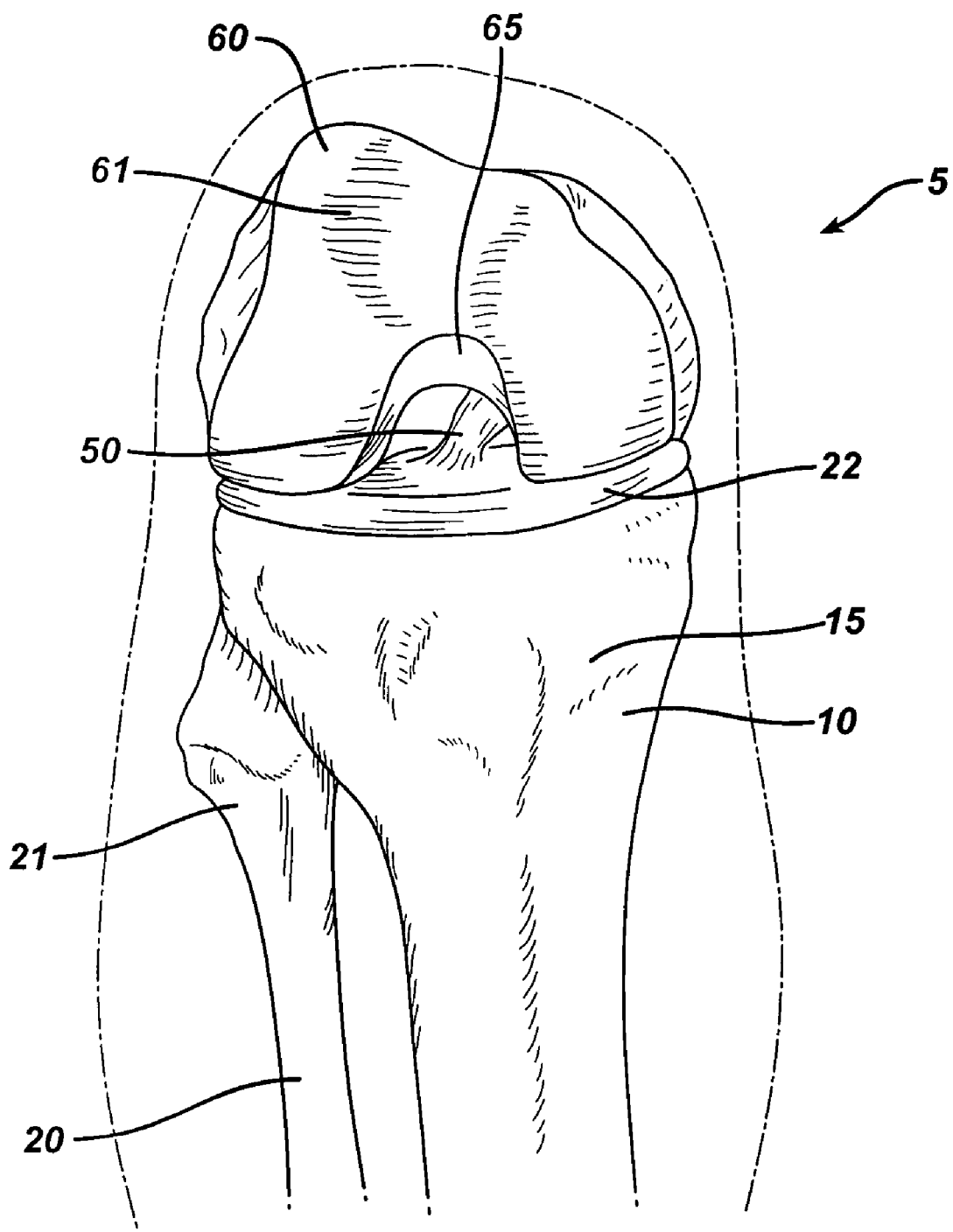
FIG. 1 is an illustration of a human knee having a ruptured anterior cruciate ligament.

Referring now to FIGS. 1-15, the novel surgical method of the present invention of replacing a ruptured anterior cruciate ligament to reconstruct a knee is illustrated. FIG. 1 illustrates a typical patient's knee 5 prior to the onset of the surgical procedure. Illustrated is the top 15 of the tibia 10, the top 21 of the fibula 20, the bottom 61 of the femur 60, as well as the condylar notch 65. The posterior collateral ligament 50 is seen to be present in the knee 5. Also seen at the top 15 of the tibia 10 the meniscal cartilage 22.

Figure 2:
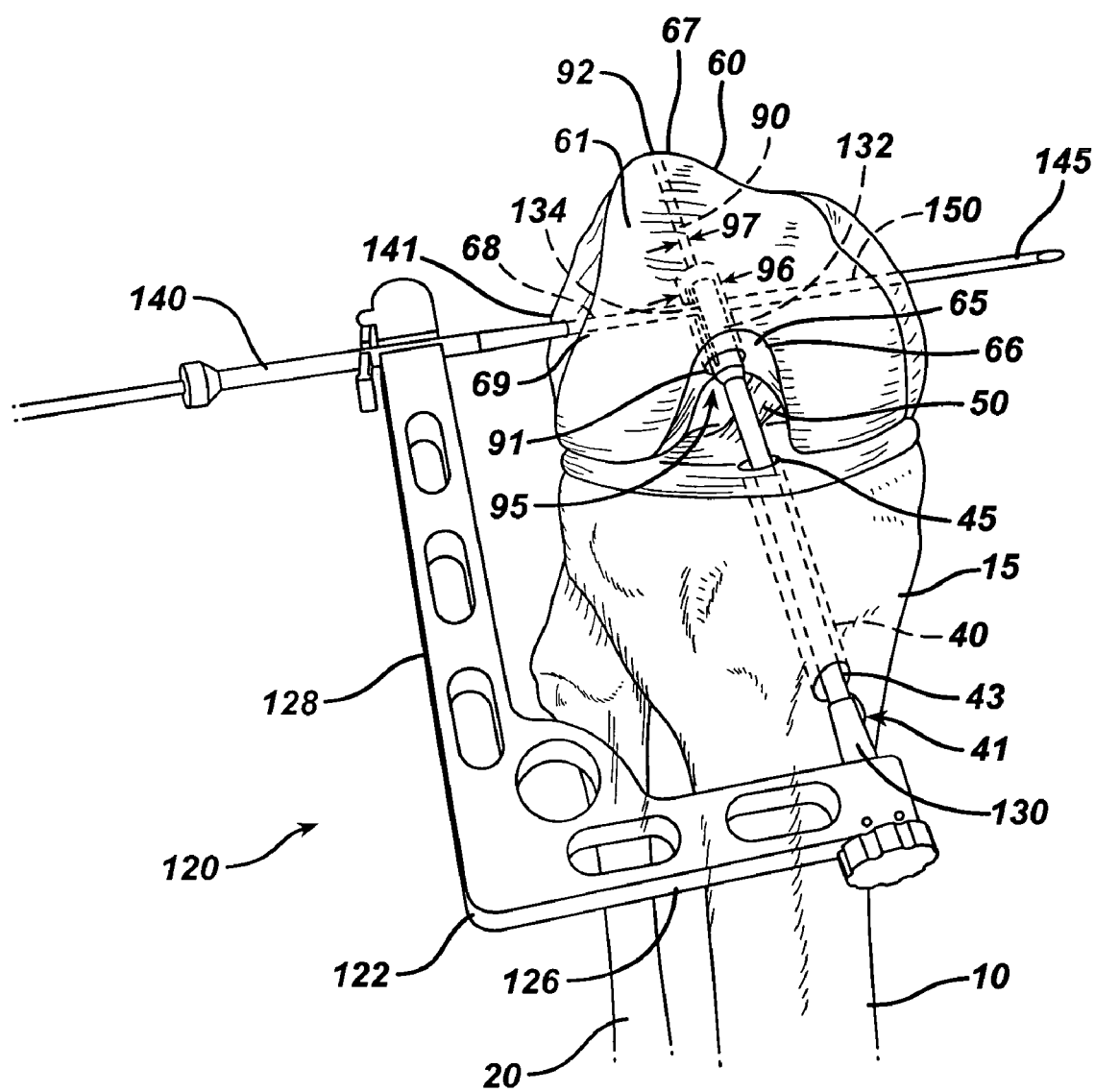
FIG. 2 is an illustration of the knee of FIG. 1 having tibial and femoral tunnels drilled in the tibia and femor respectively, and illustrating a drill guide mounted to the knee for drilling a transverse tunnel in the femor to receive a cross-pin.
Figure 3:
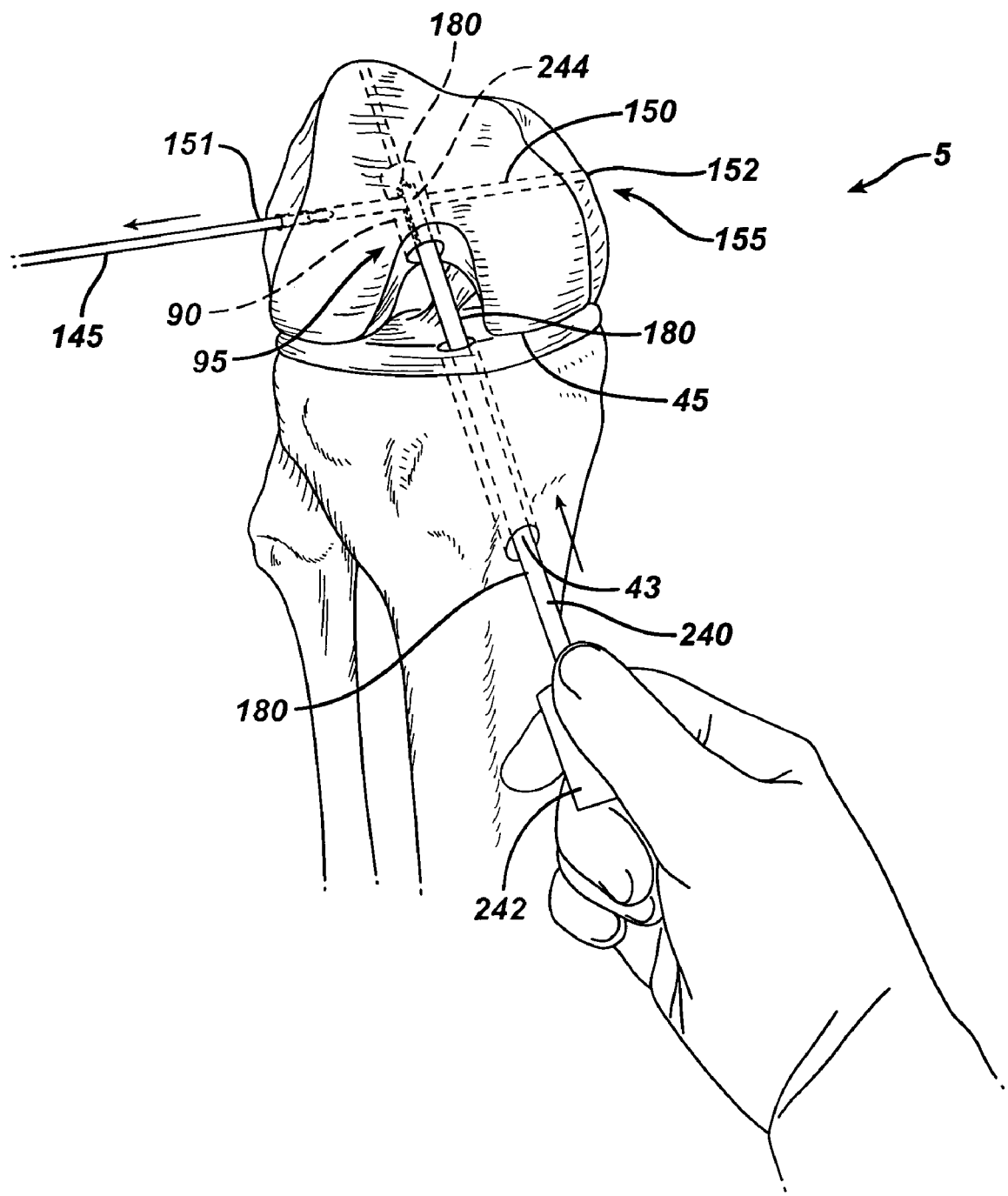
FIG. 3 illustrates an instrument for inserting a looped filamentary member into the tibial and femoral tunnels.
Figure 4:
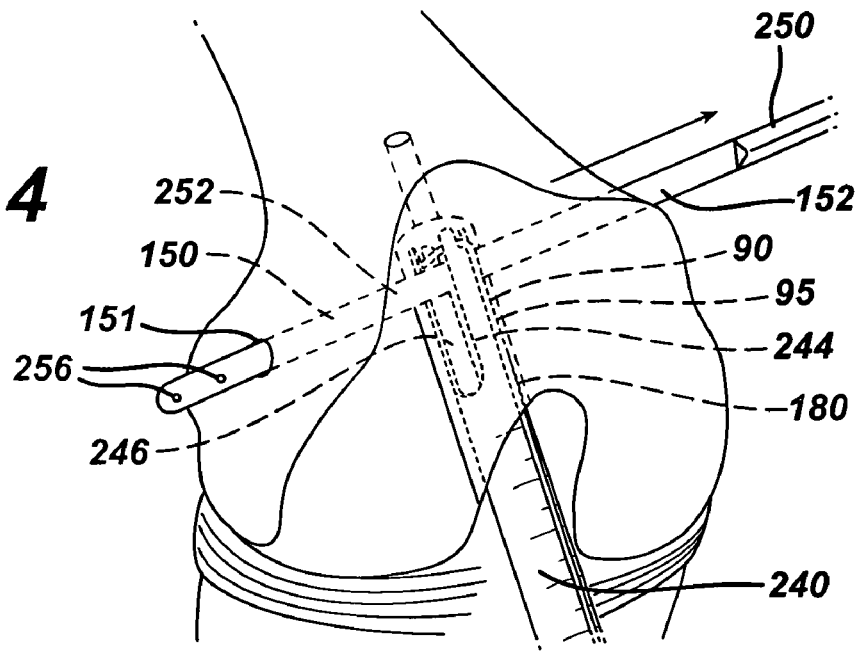
FIG. 4 illustrates the distal end of the loop insertion instrument in the femoral tunnel with a passing pin inserted into the transverse tunnel.
Figure 5:
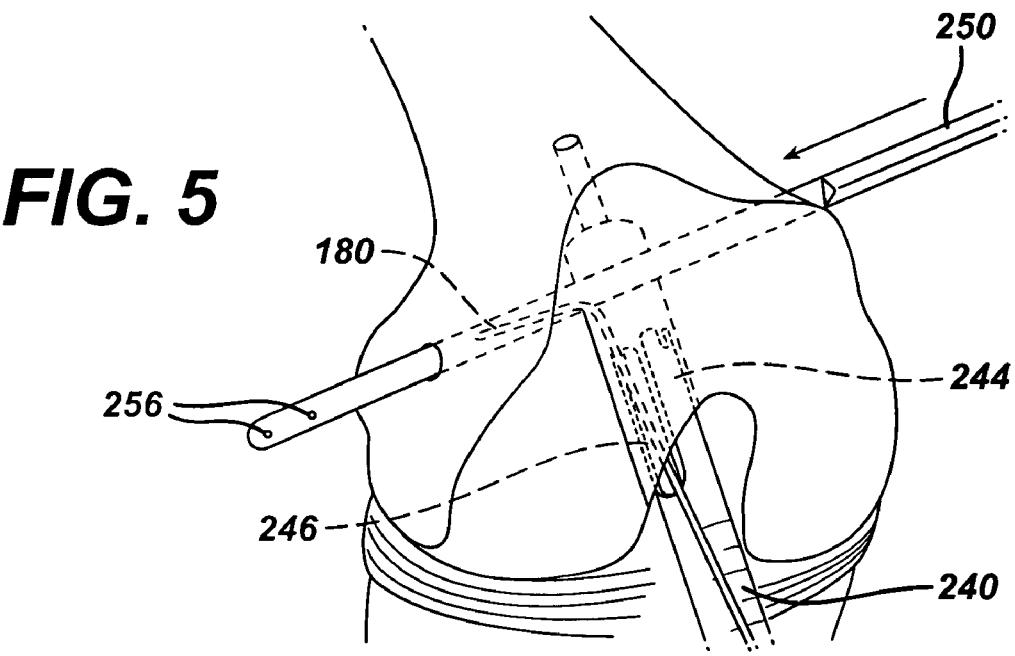
FIG. 5 illustrates the passing pin capturing a looped segment of the filamentary member from the loop insertion instrument as the loop insertion instrument is withdrawn from the femoral tunnel.
Figure 6:
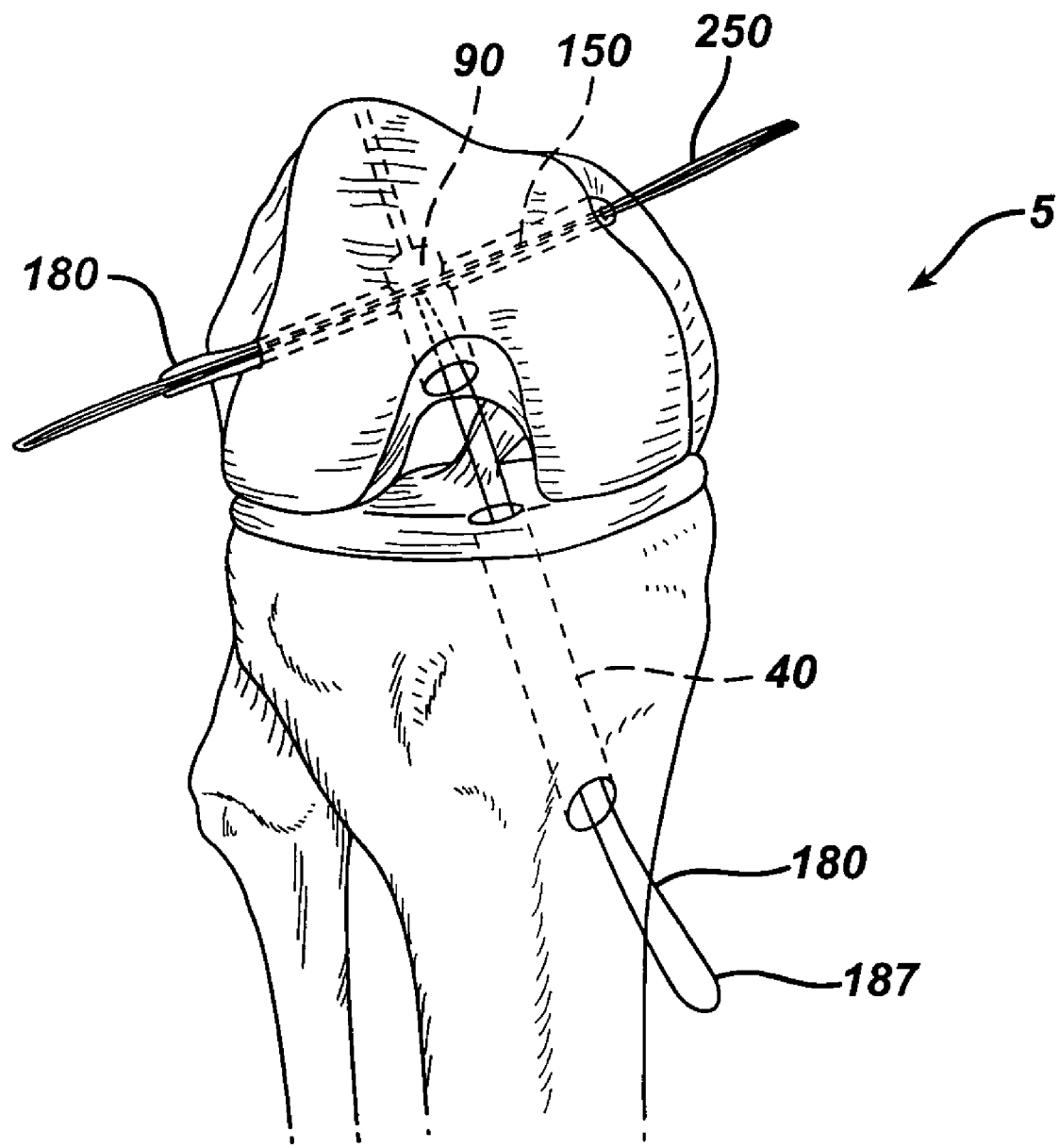
FIG. 6 illustrates the distal end of the passing pin extending out through one end of the transverse tunnel, and the loop segment exiting the transverse tunnel.
Figure 7:
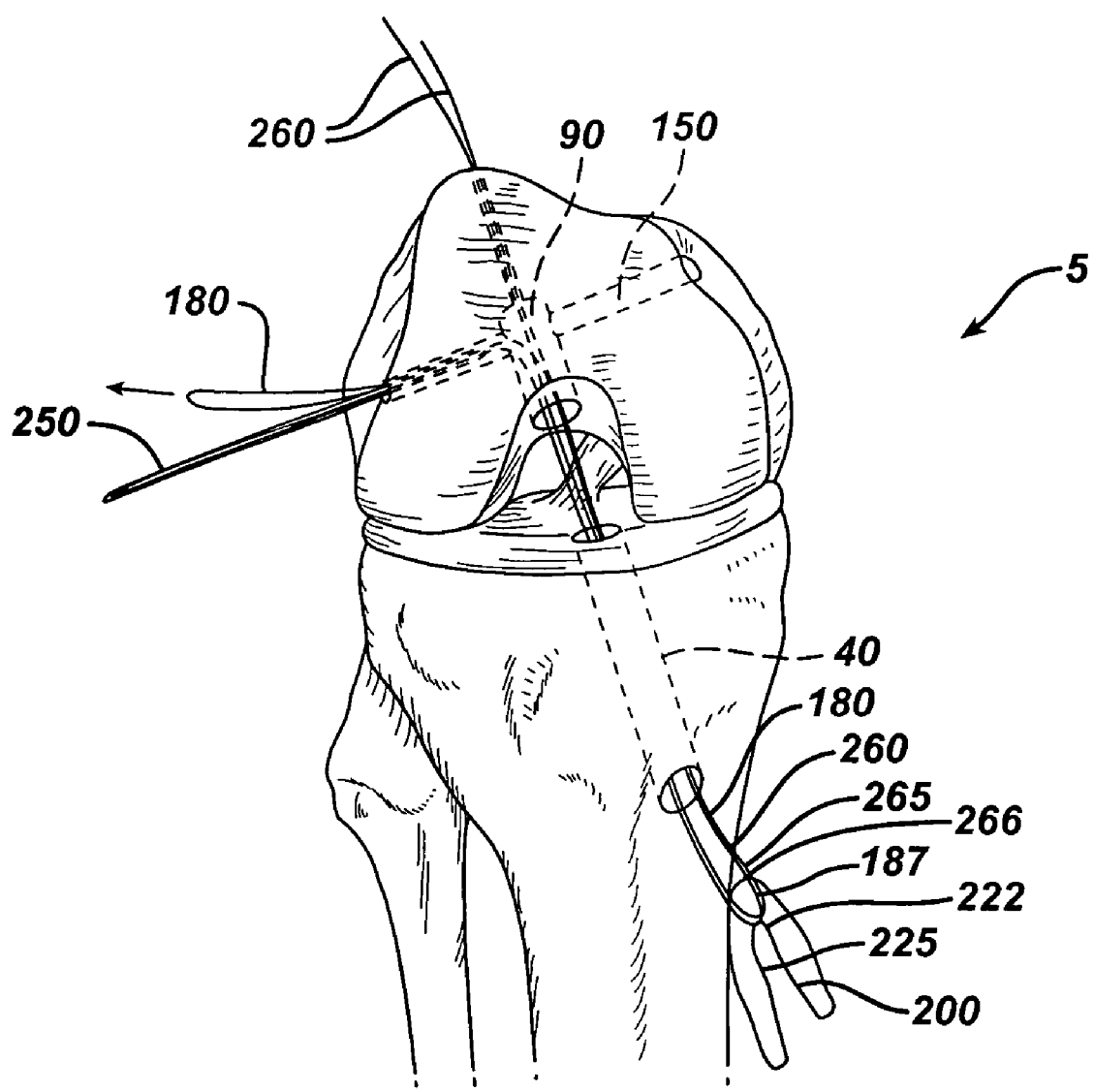
FIG. 7 illustrates the knee with a surgical suture loop threaded through the tibial and femoral tunnels, and a graft looped segments of the filamentary member and the suture extending out from the bottom of the tibial tunnel; the passing pin has been moved laterally in the transverse to a side of the femoral tunnel.
Figure 8A:
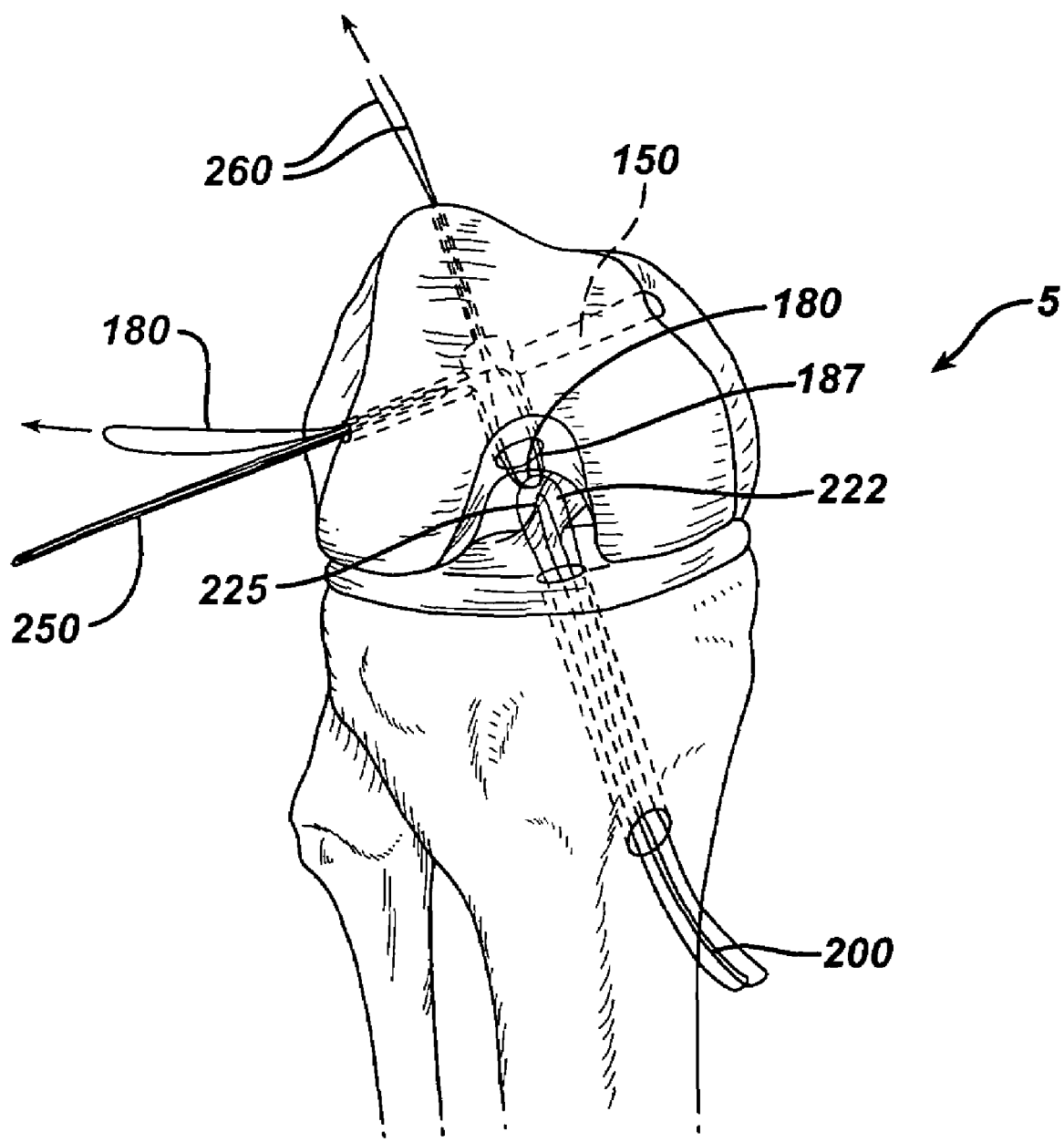
FIGS. 8a-c illustrates the graft moved into a position extending out from the tibial tunnel adjacent to the entrance to the tibial tunnel, with the top loop segment being cut with surgical scissors and one end being threaded into openings in the passing pin member.
Figure 8B:
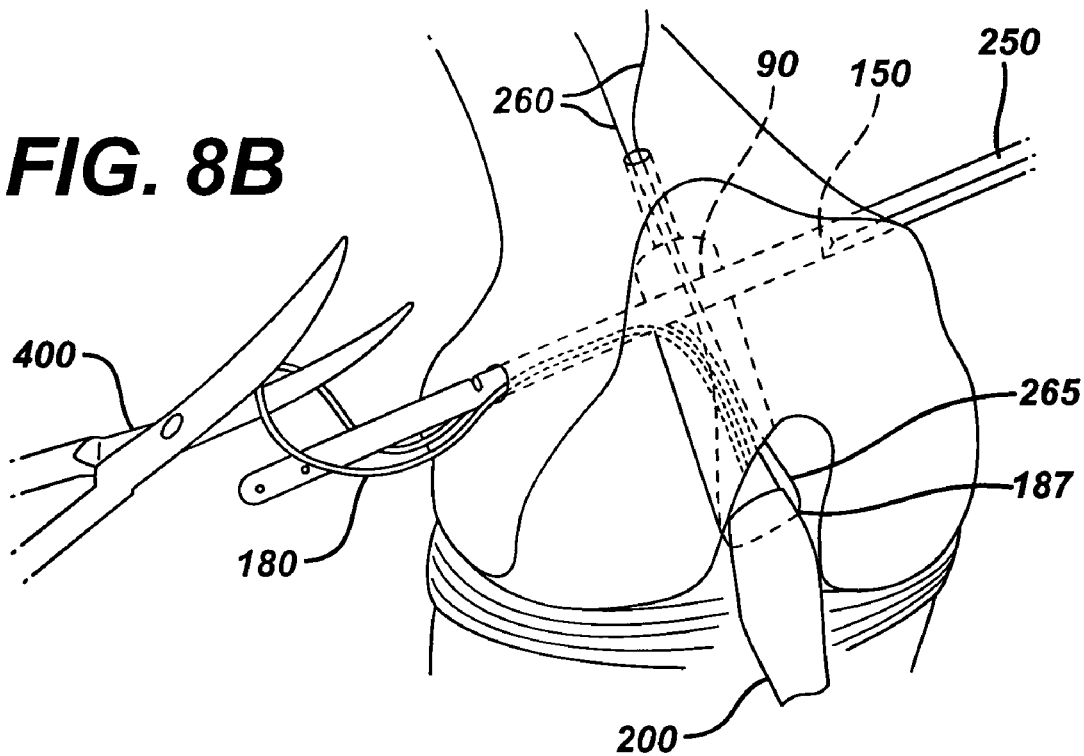
Figure 8C:
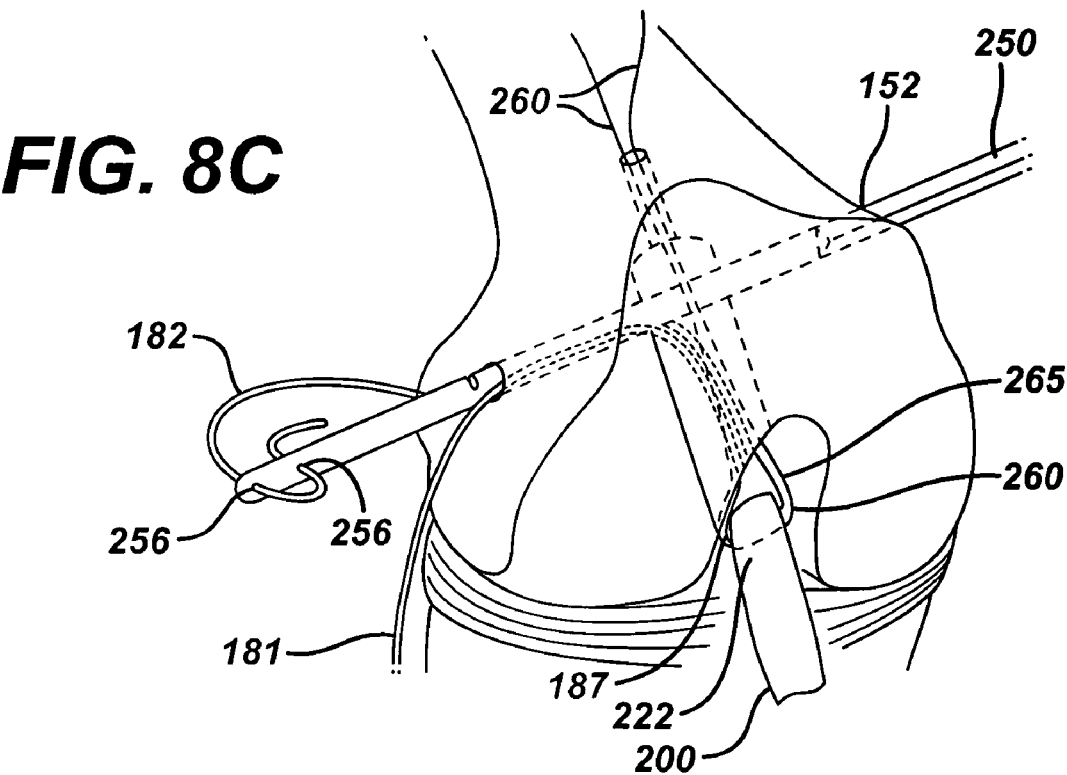
Figure 9:
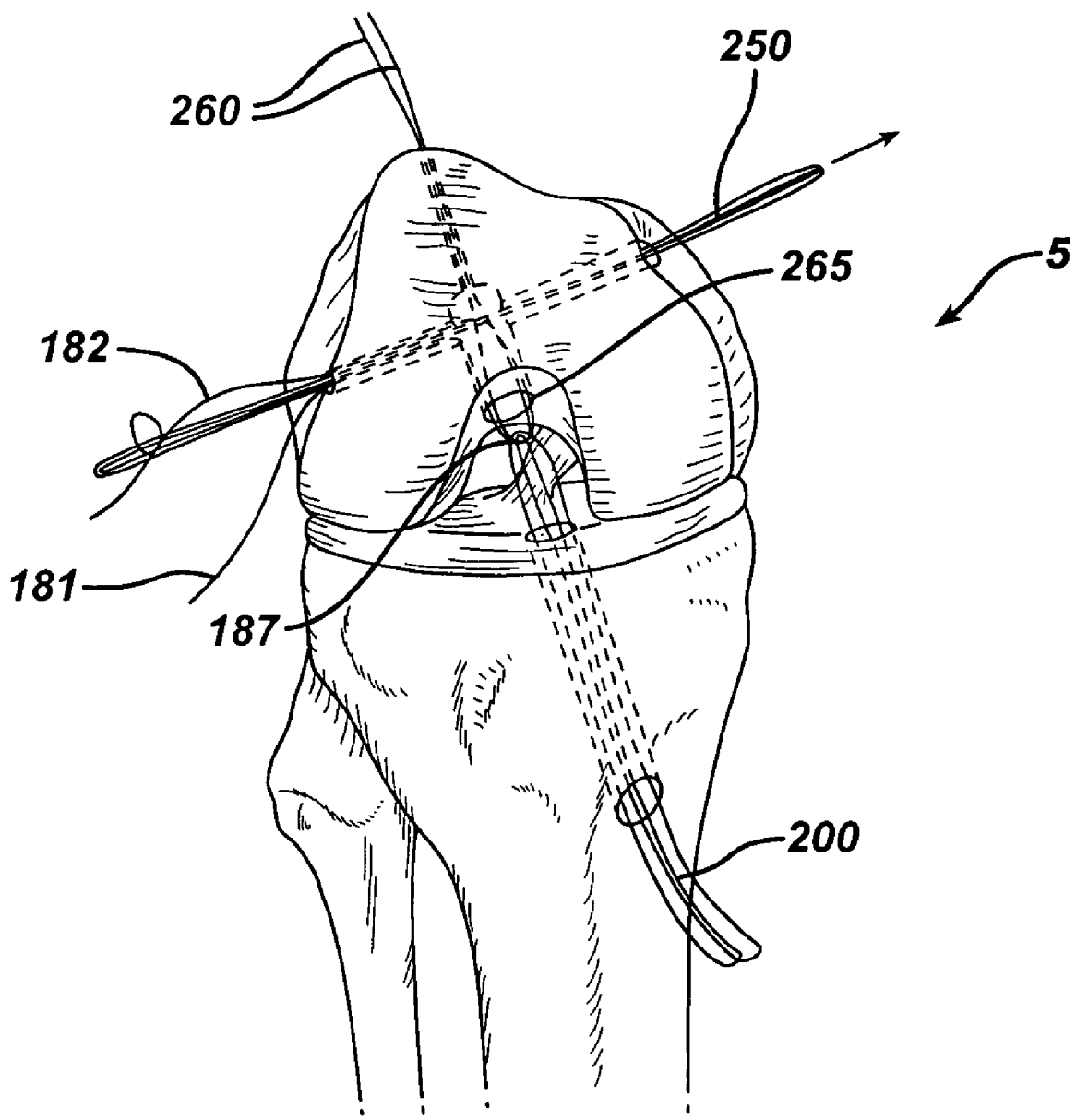
FIG. 9 illustrates the passing pin moved through the transverse tunnel, with the looped segment cut and having a first cut end mounted to the distal end of the passing pin prior to moving the passing pin and end through the transverse tunnel, while the second cut end is free.
Figure 10:
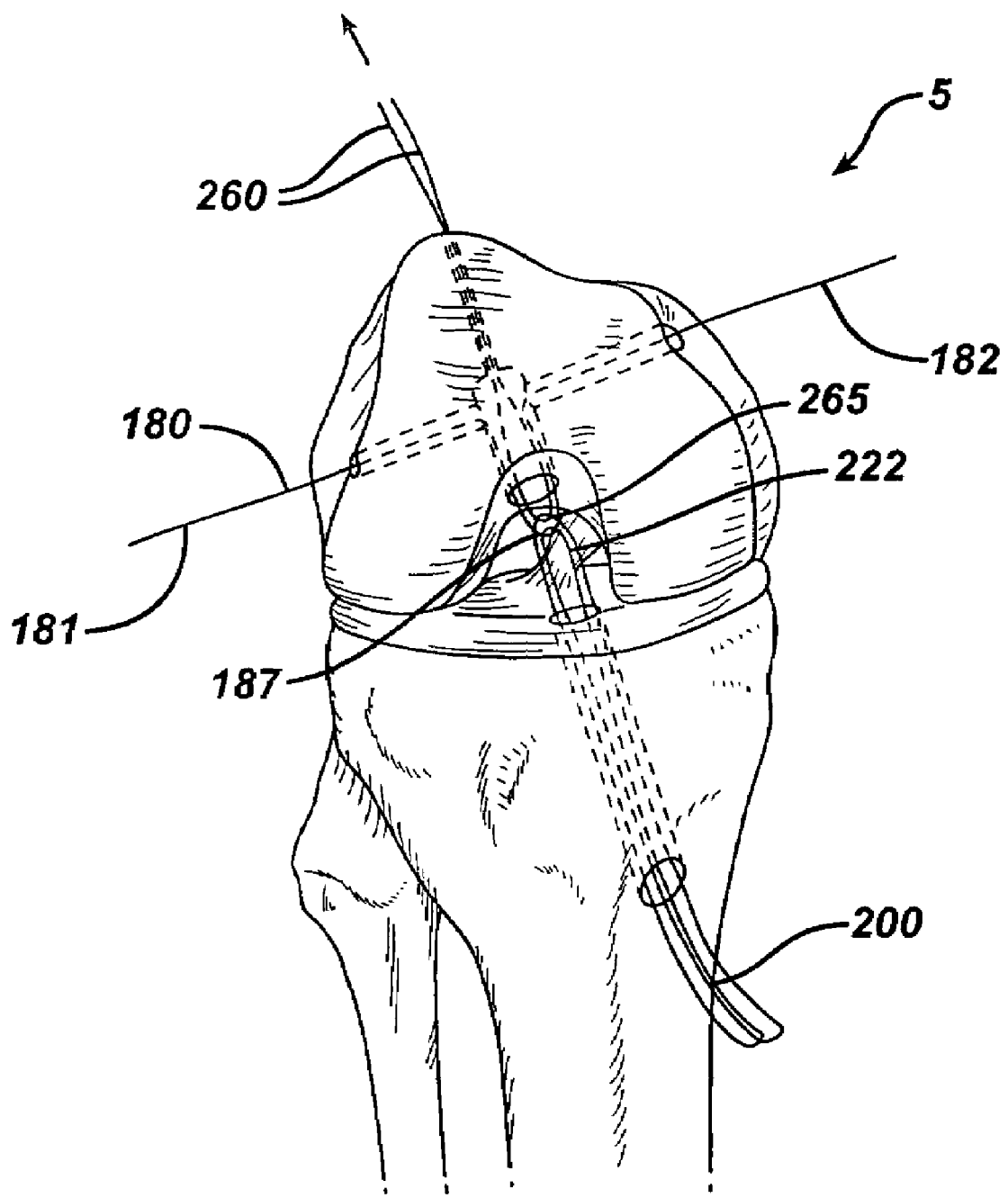
FIG. 10 illustrates the first and second ends of the filamentary member exiting opposite sides of the transverse tunnel with a bottom loop segment extending out through the bottom opening of the femoral tunnel with the top of the graft adjacent to the bottom opening of the femoral tunnel; the passing pin has been removed from the transverse tunnel.

As seen in FIG. 2, after preparing the patient's knee 5 using conventional arthroscopic surgical procedures, a tibial tunnel 40 is drilled in a conventional manner through the top 15 of the tibia 10 to create tibial tunnel 40. Tibial tunnel 40 has passage 41 having lower opening 43 and upper opening 45. The tibial tunnel 40 is drilled using a conventional two-step process with an initial pilot guide drill followed by a subsequent coring reamer to create the tibial tunnel 40 having passage 41. Preferably, the tibial tunnel is positioned in the posterior one-half of the normal attachment site of the ACL. The tunnel 40 is typically debrided of all surrounding debris at lower opening 43 and upper opening 45, and any sharp edges are chamfered using a conventional bone rasp. Next a conventional offset femoral aiming device (not shown) is inserted through opening 43 and into the tibial tunnel 40 such that the distal end of the femoral aimer device extends out through the opening 45 at the top of the tunnel 40, and the distal end of the femoral aimer device engages a suitable position on the superior rim 66 of the condylar notch 65. Then a guide pin can be drilled up through the notch 65 and out of the anterior cortex 67 of the femur 60. Next a femoral tunnel 90 is reamed out using a conventional surgical reamer to accommodate the graft diameter. The femoral tunnel 90 is seen to have bottom opening 91, passage 95 and top opening 92. The tunnel is seen to have internal step 93 where the passage 95 transitions between first diameter 96 and second diameter 97. The tunnel 90 is typically debrided of all surrounding debris at bottom opening 91 and top opening 92, and any sharp edges are chamfered using a conventional bone rasp.

Next, a transverse femoral drill guide 120 is mounted to the tibia 10 and the femur 60. The drill guide 120 is seen to have "L" shaped frame 122 having bottom leg 126 and perpendicular top leg 128. The drill guide 120 is seen to have longitudinal drill guide 130 mounted to the bottom leg 126 and horizontal drill guide 140 mounted to the top leg 128. The longitudinal drill guide 130 is positioned within the tibial and femoral tunnels 40 and 90, respectively. A partial incision 141 is made in the skin and the tissue thereunder is bluntly bisected to the lateral femoral cortex 68. The drill guide 140 is advanced to contact the lateral femoral condyral 69. Next, a drill 145 is inserted into the transverse drill guide 140 and the transverse tunnel 150 is drilled transversely through the femoral end 61. The distal end section 132 of the longitudinal drill guide 130 contains an opening 134 to receive the drill 145 to provide for appropriate alignment. The tunnel 150 is seen to have passage 155, and opposed end openings 151 and 152. The knee 5 is now ready to have the replacement ACL graft implanted.

The types of ACL implants that can be used in the method of the present invention include autografts, allografts, xenografts and synthetic grafts. Autografts consists of the patients own ligamentous tissue harvested either from the patellar tendon or from the tendons of the hamstring. Allografts include ligamentous tissue harvested from cadavers and appropriately treated and disinfected, and preferably sterilized. Xenografts include harvested connective tissue from animal sources such as, for example, porcine tissue. Typically, the xenografts must be appropriately treated to eliminate or minimize an immune response. Synthetic grafts include grafts made from synthetic polymers such as polyurethane, polyethylene, polyester and other conventional biocompatible bioabsorbable or nonabsorbable polymers and composites. The grafts 200 are typically prepared in a conventional manner, optionally whip stitching the ends 212 of the graft with surgical sutures 220, and folding the graft over by bringing the ends 212 together to form a loop of graft material having a bottom 215, a loop top 222 and a loop opening 225 as seen in FIGS. 9-14.

The filamentary members 180 that may be used in the practice of the present invention include any type of flexible, strong biocompatible material. The filaments may be a single unitary fiber or may be of multi-filament construction, for example, braided or woven. The filaments may be made from nylon, polypropylene, polyethylene, polyester, braided, woven and twisted metal and/or malleable alloys and combinations thereof. In a particularly preferred embodiment, the filamentary member 180 is made from nylon. The filamentary member 180 may be precut with two opposed ends, or may be in the form of an endless loop. It is particularly preferred in the practice of the present invention to utilize the filamentary member in the form of an endless loop that is later cut to provide a filamentary member with two ends.

When using a filamentary member 180 in the surgical method of the present invention it is preferably used in the form of an endless loop (see FIGS. 3-11). The filamentary member is loaded on to an inserter instrument 240 having a proximal handle 242 and a distal notched end 244 for engaging the loop. The distal notched end 244 of the inserter 240 having the filamentary member 180 mounted thereto is then inserted into the bottom opening 43 of the tibial tunnel 40 and the instrument is moved forward through the passage 41 of tibial tunnel 40, out of upper opening 45, through bottom opening 91 of femoral tunnel 90 and into the passage 95 of femoral tunnel 90 adjacent to the intersection with the transverse tunnel 150. Then, a passing pin member 250 is inserted into opening 152 of the transverse tunnel. The passing pin 250 is seen to have a notch 252 for receiving and engaging a section of the filamentary loop member 180. The passing pin 250 is seen to pass through opening 246 in notched end 244. Once a section of the member 180 is engaged or captured in the notch 252, the inserter member 240 is withdrawn from the femoral and tibial tunnels 40 and 90, respectively, and the shuttle instrument 250 is moved laterally until the notch 252 and the engaged section of the filamentary member 180 exits opening 151 of the transverse tunnel 150. At that time, the first top loop section 185 of member 180 is removed from the notch 252 by the surgeon and is maintained outside of opening 151. the bottom loop section 187 of the filamentary member 180 is seen to extend down out through the bottom of the tibial tunnel 40 through opening 43. A surgical suture 260 is then used to move the graft 200 into place in the tibial and femoral tunnels 40 and 90, respectively. The surgeon loops or folds the graft 200 through the opening 266 of suture loop 265 of suture 260 connected to the proximal end 282 of the straight surgical needle 280. Needle 280 has distal end 285. The suture passes through the eyelet 283 of the needle 280. At the same time the tendon graft 200 is also looped through the opening 186 of bottom section loop 187 of the filamentary member 180. The surgeon then pulls the straight surgical needle 280 up in the direction along the longitudinal axes of the femoral and tibial tunnels 40 and 90, respectively, such that the needle 280 exits the femoral tunnel 90 through top opening 92, and the suture loop pulls the distal or top end 222 of the graft loop 200 out of the tibial tunnel and adjacent to opening 91 of femoral tunnel 90. As the suture 260 pulls the distal end 222 of the graft 200 into and out of the tunnel 40, the looped end 185 of the filamentary member 180 also moves with the top end 222 of graft 200 into the space adjacent to the opening 91 of femoral tunnel 90.

Next, the surgeon cuts the top loop section 185 with conventional surgical scissors 400 to form ends 181 and 182. End 182 of the member 180 is then threaded into the eyelets 256 and the passing pin member 250 is moved horizontally in the opposite direction through passage 155 of transverse tunnel 150 exiting the transverse tunnel through opening 152 on the opposite side of tunnel 150 such that the end 182 also exits the tunnel, and the ends 181 and 182 of the filamentary member 180 exit through opposite sides of the transverse tunnel 150 (through openings 151 and 152, respectively). The passing pin member 250 is removed from the transverse tunnel 150. Needle 280 and suture 260 are then tensioned and moved through femoral tunnel 90 such that the top section of graft 200 is moved into femoral tunnel 90 and the graft top end 222 is located in the femoral tunnel 90 in a fixation position, with opening 225 in alignment with passage 155. The ends 181 and 182 of the filamentary member 180 are tensioned to place the filamentary member 180 in a straight configuration to serve as a guide wire through transverse tunnel 150 and through graft opening 225 for a conventional cannulated cross-pin.

Figure 11:
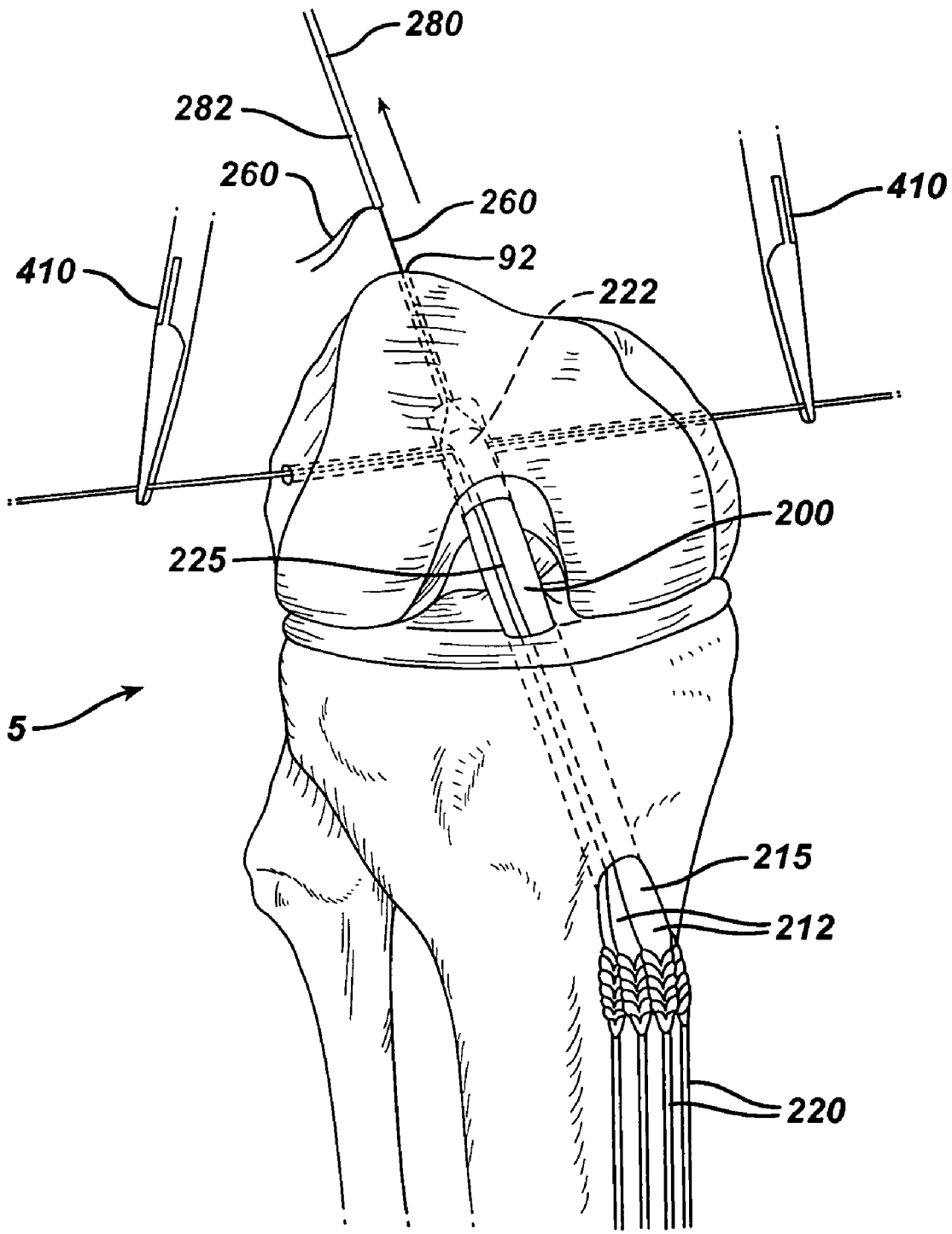
FIG. 11 illustrates a section of the suture exiting the femoral tunnel with the graft member moved into and positioned within both the femoral and tibial tunnels, having the top end of the graft emplaced in the femoral tunnel such that the graft loop opening adjacent to the transverse tunnel. Also shown is the filamentary member being tensioned to straighten and align it with the transverse tunnel to serve as a guide wire.
Figure 12:
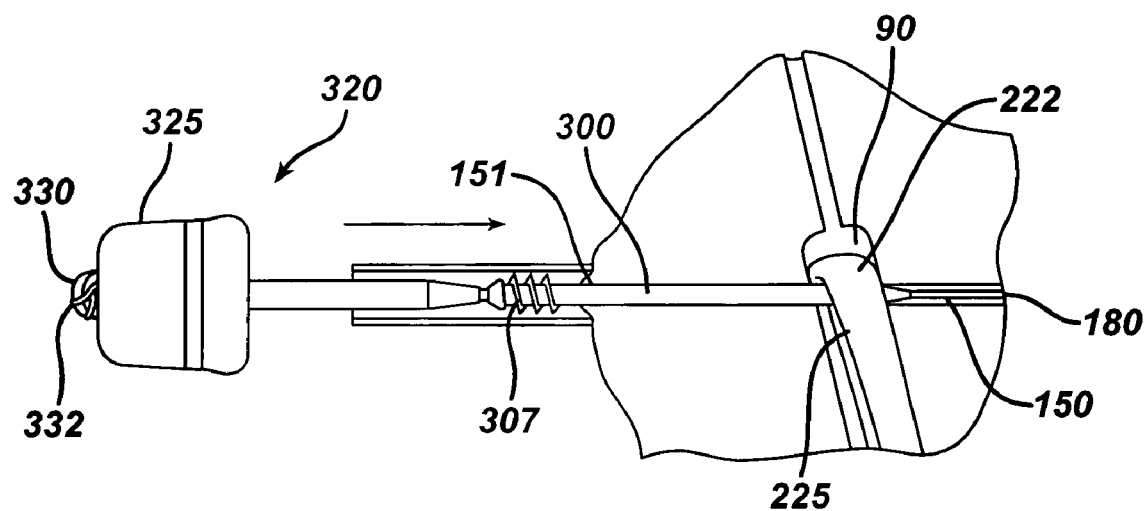
FIG. 12—illustrates a cannulated cross-pin inserted over the guide wire and partially inserted into the transverse tunnel.
Figure 13:
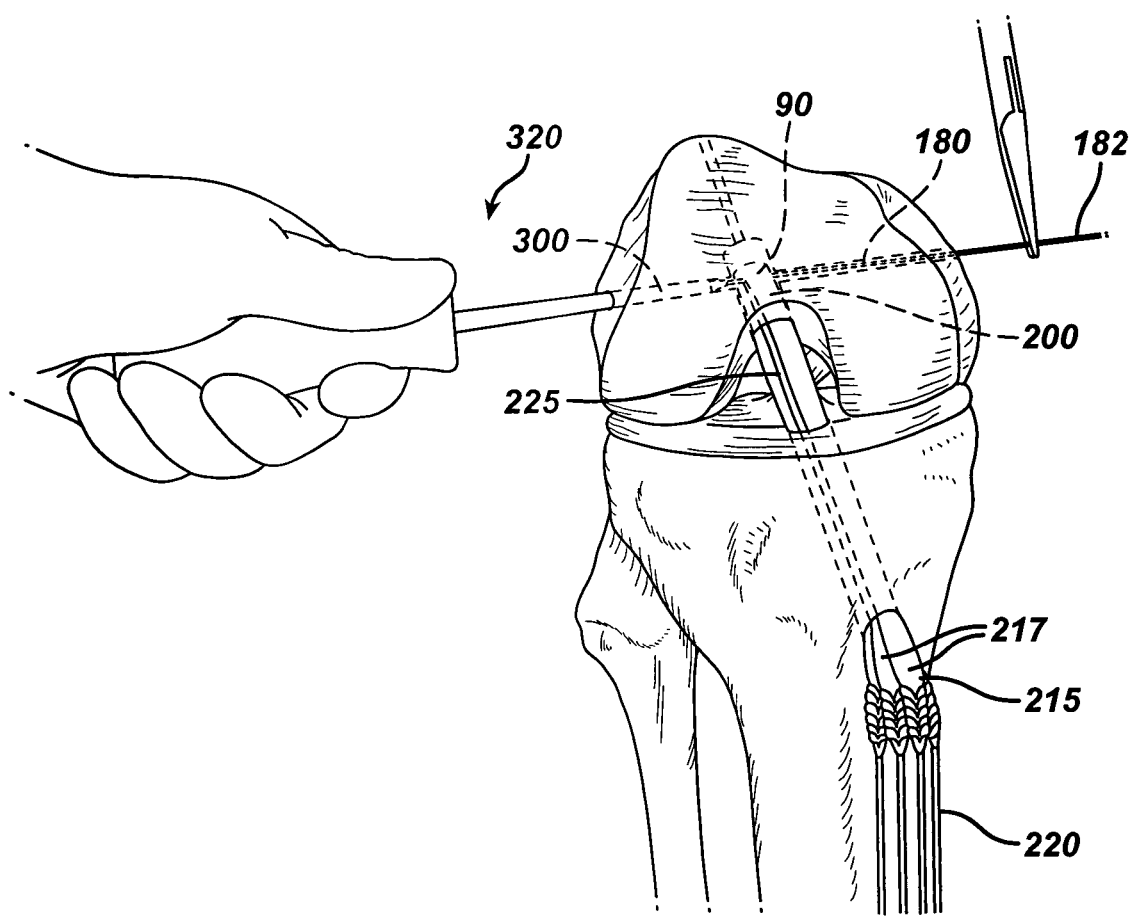
FIG. 13 illustrates the cross-pin partially inserted with the distal end in the graft loop opening and underneath the top of the graft loop.
Figure 14:
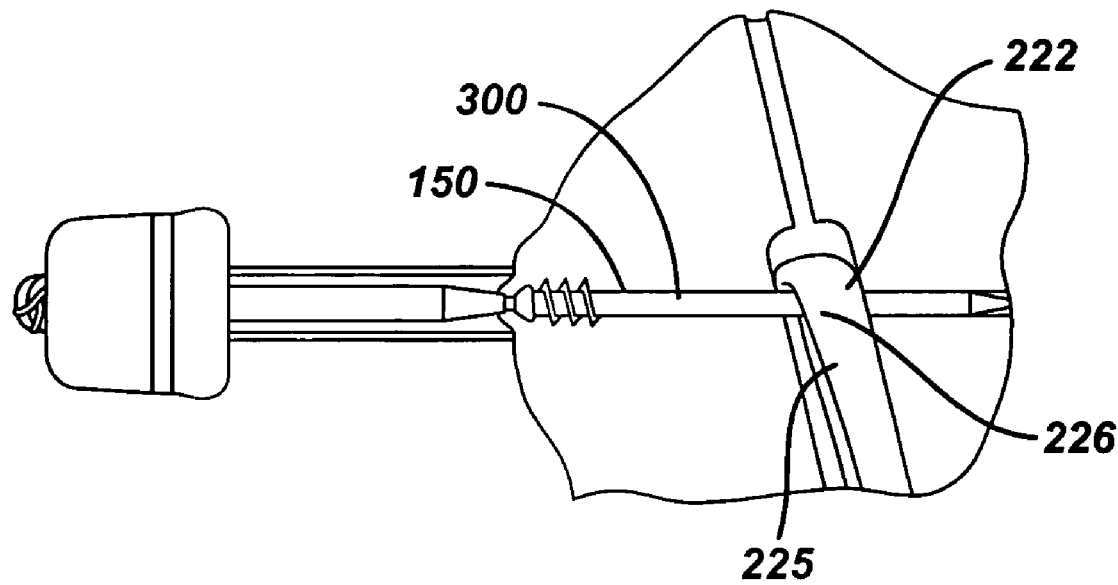
FIG. 14 illustrates the cannulated pin completely screwed into place and engaging the graft and securing the upper end of the graft in a substantially fixed position in the femoral tunnel.
Figure 15:
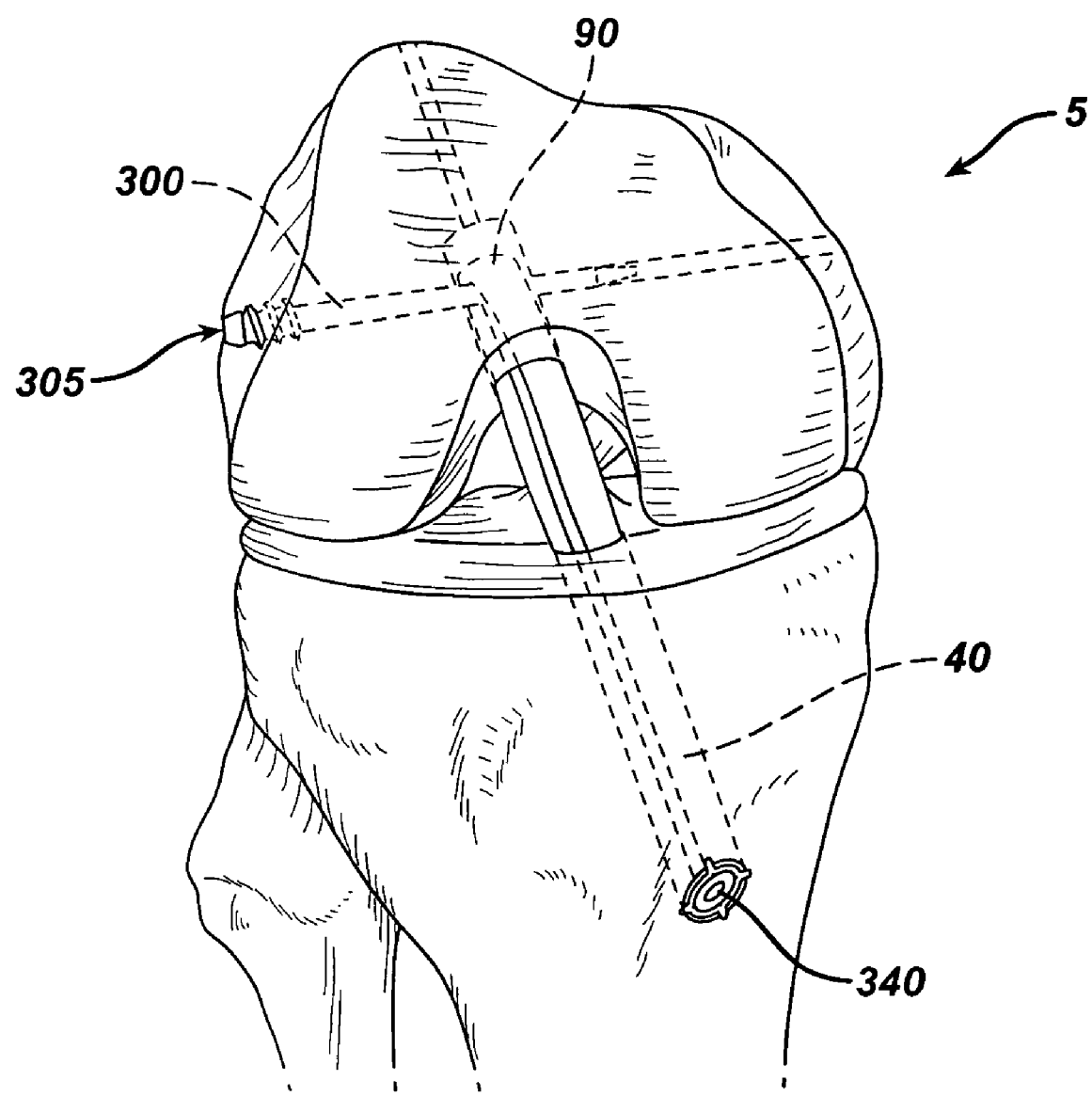
FIG. 15 illustrates the knee after the top end of the end of the graft has been secured in the femoral tunnel and the guide wire removed, and with the bottom end of the graft secured in the tibial tunnel using an interference screw, thereby completing the ACL replacement surgical procedure with the ACL replacement graft secured in both the femoral and tibial tunnels to provide for a reconstructed ACL.

Referring now to FIGS. 12-15, the cross-pin 300 is seen to have lumen 305 and threaded bone engaging section 307. The end 181 of the filamentary member 180 is threaded through lumen 305 of cannulated cross-pin 300, and secured in the handle 325 of the driving instrument 320 by attachment to the optional bead member 330 having passages 332 for receiving the end 181. Bead member 330 is mounted to the end of handle 325. The other end 182 of the filamentary member 180 is placed in tension by the surgeon while the surgeon screws the cross-pin into the tunnel 150 underneath the top 222 of the graft loop 200 and through opening 225 thereby securing the upper section of the graft 200 in the femoral tunnel 90. The surgeon then removes the driving instrument 320 from the cross-pin 300, and removes the instrument 320 and filamentary member 180 from the transverse tunnel 150 and the cross-pinning procedure is complete, with the top end 222 of the ACL replacement graft 220 substantially secured or fixed in femoral tunnel 90. Shown if FIG. 11 is the optional depth stop sleeve 390 used to assure the surgeon that the threads 307 are flush against the lateral femoral cortex 68 or slightly buried.

The surgeon then affixes the bottom end 215 of the graft 200 in the tibial tunnel 40 using a conventional securing device such as an interference screw 340, or other conventional devices such as tibial fasteners, screws and washers, etc. The ACL replacement is now complete, and the surgeon can remove the cannulas and close the incisions about the knee using conventional incision approximating techniques including sutures, tape, glue, staples, etc.

The cross-pins useful in the present invention can be made from a variety of conventional biocompatible materials useful in implants. The materials may be absorbable or non-absorbable. Examples of conventional non-absorbable materials include surgical stainless steel, nickel titanium alloys, ceramics, Delrin, polyethylene, and other non-absorbable polymers including, but not limited to, polypropylene, and Acetal. Examples of bioabsorbable materials include PLA, PGA, polydioxanone, polycaprolactone, copolymers thereof, and the like. The term "natural polymer" refers to polymers that are naturally occurring, as opposed to synthetic polymers. In embodiments where the device includes at least one synthetic polymer, suitable biocompatible synthetic polymers can include polymers selected from the group consisting of aliphatic polyesters, poly(amino acids), copoly(etheresters), polyalkylenes oxalaes, polyamides, tyrosine derived polycarbonates, poly(iminocarbonates), polyorthoesters, polyoxaesters, polyamidoesters, polyoxaesters containing amine groups, poly(anhydrides), polyphosphazenes, polyurethanes, poly(ether urethanes), poly(ester urethane) and blends thereof. Suitable synthetic polymers for use in the present invention can also include biosynthetic polymers based on sequences found in collagen, elastin, thrombin, fibronectin, starches, poly(amino acid), poly(propylene fumarate), geletin, alginate, pectin, fibrin, oxidized cellulose, chitin, chitosan, tropoelastin, hyaluronic acid, ribonucleic acids, deoxyribonucleic acids, polypeptides, proteins, polysaccharides, polynucleotides and combination thereof. The devices of the present invention may also be manufactured from conventional biocompatible natural polymers. If desired, the bioabsorbable materials may contain osteoinductive or osteoconductive materials, polymers and blends of polymers including but not limited to calcium hydroxyapatite, tricalcium phosphate, and the like.

The cross-pins of the present invention may be made using a variety of conventional manufacturing processes including machining, molding, etc., and combinations thereof.

The novel anterial cruciate ligament replacement procedure of the present invention has improvements over procedures known in the art. In particular, the combination of the needle and suture to pull the graft into the femoral tunnel along with the suture loop filamentary member to provide for a transverse guide wire provides efficiency in the placement of the top of the graft in the femoral tunnel while minimizing or eliminating damage to the bone in the transverse tunnel that could be caused by pulling up the graft using the filamentary member. At the same time that the graft is emplaced in the femoral tunnel, the filamentary wire is in place in the transverse tunnel to serve as a guide wire for emplacing the cross-pin in the transverse tunnel and through the opening in the graft loop.

Although this invention has been shown and described with respect to detailed embodiments thereof, it will be understood by those skilled in the art that various changes in form and detail thereof my be made without departing form the spirit and scope of the claimed invention.

We claim:

1. A method of repairing a knee, comprising:

providing an anterior cruciate ligament replacement graft having opposed ends;

drilling a longitudinal tibial tunnel through a top section of a tibia, the tibial tunnel having a top opening and a bottom opening;

drilling a longitudinal femoral tunnel through a bottom section of an adjacent femur such that the tibial tunnel and the femoral tunnel are substantially in alignment, wherein said femoral tunnel has a bottom opening and a top opening;

drilling a substantially transverse tunnel through the femoral tunnel, such that the transverse tunnel intersects the femoral tunnel, and is in communication therewith, the transverse tunnel having first and second open ends;

providing a filamentary member, wherein said filamentary member comprises an endless loop;

threading the filamentary member through the knee such that a first loop segment of the filamentary member extends out from one end of the transverse tunnel and a second loop segment of the filamentary member extends out through a bottom opening of the tibial tunnel;

providing a surgical needle and attached surgical suture;

folding the graft to form a graft loop having a top, a bottom, and an opening;

engaging the graft with the suture such that the suture passes through the graft loop opening;

engaging the graft with the filamentary member such that it passes through the graft loop opening;

pulling the graft loop up and into the tibial tunnel by pulling on the needle and suture, such that the top of the graft is outside of the tibial tunnel adjacent to the bottom opening of the femoral tunnel, and the second loop segment of the filamentary member is also outside of the tibial tunnel; adjacent to the bottom opening of the femoral tunnel cutting the first loop segment of the filamentary member to form first and second ends, and manipulating the filamentary member to extend completely through the transverse tunnel such that the first end of the filamentary member extends out from the first open end of the transverse tunnel and the second end of the filamentary member extends out from the opposed second open end of the transverse tunnel;

pulling the top section of the graft into the femoral tunnel by pulling on the needle and suture such that the graft loop opening is in alignment with the transverse tunnel;

manipulating the filamentary member such that it is tensioned to form a substantially straight configuration that is substantially in alignment with the transverse tunnel;

providing a cannulated bone cross-pin having an outer surface; and, securing the upper end of the graft loop in the femoral tunnel by passing the cannulated cross-pin over the filamentary member and through the graft loop opening, and mounting the cross-pin in the transverse tunnel.

2. The method of claim 1 additionally comprising the steps of providing a tibial securement member and securing the lower end of the graft loop in the tibial tunnel by inserting the securement member into the tibial tunnel.

3. The method of claim 1 wherein the cannulated cross-pin comprises at least one section of threads on its outer surface.

4. The method of claim 1, wherein the cannulated cross-pin comprises an absorbable polymer.

5. The method of claim 1, wherein the cannulated cross-pin comprises a biocompatible metal.

6. The method of claim 1, wherein the cannulated cross-pin comprises a biocompatible material selected from the group consisting of allograft bone, autograft bone, ceramics and composites.

* * * * *